US012582832B2

(12) United States Patent
Gerstenmeier

(10) Patent No.: US 12,582,832 B2
(45) Date of Patent: Mar. 24, 2026

(54) DEVICE FOR APPLYING MEDICAL AND COSMETIC RADIATION TO A HUMAN BODY OR TO PARTS OF A HUMAN BODY

(71) Applicant: JK-HOLDING GMBH, Windhagen (DE)

(72) Inventor: Jürgen Gerstenmeier, Neuwied (DE)

(73) Assignee: JK-Holding GmbH, Windhagen (DE)

( * ) Notice: Subject to any disclaimer, the term of this patent is extended or adjusted under 35 U.S.C. 154(b) by 674 days.

(21) Appl. No.: 17/999,428

(22) PCT Filed: May 21, 2021

(86) PCT No.: PCT/IB2021/054434
§ 371 (c)(1),
(2) Date: Nov. 21, 2022

(87) PCT Pub. No.: WO2021/240326
PCT Pub. Date: Dec. 2, 2021

(65) Prior Publication Data
US 2023/0233870 A1     Jul. 27, 2023

(30) Foreign Application Priority Data
May 25, 2020    (CH) .................................... 00614/20

(51) Int. Cl.
*A61N 5/06*          (2006.01)
*A61L 2/10*          (2006.01)
(Continued)

(52) U.S. Cl.
CPC .............. *A61N 5/0613* (2013.01); *A61L 2/10* (2013.01); *A61L 2/26* (2013.01); *A61L 9/12* (2013.01);
(Continued)

(58) Field of Classification Search
CPC ...... A61L 2/0047; A61L 2/26; A61L 2202/11; A61L 2209/12; A61L 2209/14;
(Continued)

(56) References Cited

U.S. PATENT DOCUMENTS

2009/0179547 A1     7/2009  Auday et al.

FOREIGN PATENT DOCUMENTS

CN          1296420  A     5/2001
CN          103691070 A     4/2014
(Continued)

OTHER PUBLICATIONS

Japan Patent Office, Notice of Reasons for Rejection issued in JP Application 2022-571107, mailed Dec. 3, 2024. 10 pages (w/translation).
(Continued)

*Primary Examiner* — Amanda K Hulbert
(74) *Attorney, Agent, or Firm* — HESLIN ROTHENBERG FARLEY & MESITI P.C.

(57) ABSTRACT

The present invention relates to a device for applying medical and cosmetic radiation to a human body or to parts thereof. Said radiation is preferably optical radiation. The device according to the invention comprises at least one first illuminant for producing the medical and cosmetic radiation. The device also comprises a first air flow for cooling an illuminant and a second air flow for cooling the human body or parts thereof. The device comprises at least one air-conditioning system, which is fluidically connected to the second air flow and designed for the air-conditioning treatment of the air flow. The device is characterized in that the device also has at least one disinfecting chamber, which is fluidically connected to the second air flow and is designed to physically disinfect the second air flow. The invention
(Continued)

also relates to a method for operating such a device and to a corresponding disinfecting chamber.

20 Claims, 5 Drawing Sheets

(51) Int. Cl.

| | |
|---|---|
| *A61L 2/26* | (2006.01) |
| *A61L 9/12* | (2006.01) |
| *A61L 9/20* | (2006.01) |
| *A61L 103/05* | (2026.01) |
| *A61N 5/00* | (2006.01) |

(52) U.S. Cl.

CPC ............. *A61L 9/20* (2013.01); *A61L 2103/05* (2026.01); *A61L 2202/11* (2013.01); *A61L 2209/12* (2013.01); *A61L 2209/14* (2013.01); *A61L 2209/16* (2013.01); *A61N 2005/005* (2013.01); *A61N 2005/007* (2013.01)

(58) Field of Classification Search

CPC .......... A61L 2209/16; A61L 9/12; A61L 9/20; A61N 2005/005; A61N 2005/007; A61N 2005/0615; A61N 2005/0661; A61N 2005/0665; A61N 5/0613; A61N 5/0614; A61N 5/0618

See application file for complete search history.

(56) References Cited

FOREIGN PATENT DOCUMENTS

| | | |
|---|---|---|
| CN | 106178279 A | 12/2016 |
| DE | 4119793 A1 | 12/1992 |
| DE | 19602018 A1 | 7/1997 |
| DE | 202005009283 U1 | 10/2005 |
| JP | 2016032620 A | 3/2016 |
| JP | 2018532524 A | 11/2018 |
| WO | 2007051141 A2 | 5/2007 |
| WO | 2020016436 A1 | 1/2020 |

OTHER PUBLICATIONS

International Search Report and Written Opinion of International Application No. PCT/IB2021/054434, mailed Aug. 19, 2021, 15 pages.

DEVICE FOR APPLYING MEDICAL AND COSMETIC RADIATION TO A HUMAN BODY OR TO PARTS OF A HUMAN BODY

CROSS REFERENCE TO RELATED APPLICATIONS

This application is a U.S. National Phase filing under 35 U.S.C. § 371 of International Application PCT/IB2021/054434, filed May 21, 2021, and published as WO 2021/240326 A1 on Dec. 2, 2021. PCT/IB2021/054434 claims priority from Swiss application number CH 00614/20, filed May 25, 2020. The entire contents of each of these prior applications are hereby incorporated herein by reference.

The present invention relates to a device for acting on a human body or portions of a human body with medical-cosmetic radiation.

The invention further relates to a method for operating such a device, and to a disinfection chamber for upgrading such devices, all according to the preambles of the independent claims.

TECHNOLOGICAL BACKGROUND

Devices for acting on a human body or portions of a human body with medical-cosmetic radiation include tanning beds, for example, via which tanning of the skin is to be achieved for cosmetic reasons. In addition, such devices also include devices that are used for medical purposes, wherein a human body is acted on with medical-cosmetic radiation, for example to treat skin diseases. Furthermore, devices may be understood as devices which are to create a psychosomatic effect by acting on a human body or portions of a human body with light.

For all these devices, both for cosmetic and for medical purposes, a completely hygienic environment is expected by the users. With tanning beds, cleaning aspects such as the accessibility and washability of surfaces are therefore also always taken into account. During use, excretions by the human body or portions of the human body may result in an adverse hygienic impact on the device. Accordingly, the commercially available devices of the type mentioned at the outset are designed so that they are easy to clean.

For many of the stated devices, in addition to the tanning effect, considerable heat generation occasionally occurs. This is due on the one hand to the electrical mode of operation of the illuminants used, and on the other hand to the action by the optical radiation in question on the skin. Although a certain amount of heat generation may be desirable, most devices are additionally equipped with ventilation and/or cooling, which cool(s) the user during use. In conjunction with this cooling, hygienic issues regarding possible bacterial load also arise, for the cosmetic tanning sector as well as for the medical-therapeutic field of application.

For the users in the cosmetic as well as medical sectors, it is desirable for users to be able to rely on a completely hygienic environment and treatment. Therefore, there is a need for devices of the type stated at the outset which are able to meet high hygienic demands.

DESCRIPTION OF THE INVENTION

Therefore, the object of the present invention is to provide a device for acting on a human body or portions of a human body with medical-cosmetic radiation, which with regard to known devices has better hygienic properties. In particular, the aim is to provide such a device as well as a method for operating such a device, and a means for upgrading existing devices, which are easy and safe to use and which improve the hygiene without further effort for the user.

The stated object is achieved using a device for acting on a human body or portions of a human body with medical-cosmetic radiation according to the characterizing part of the independent claims.

One aspect of the present invention relates to a device for acting on a human body or portions of a human body with medical-cosmetic radiation.

Within the meaning of the present invention, the optical radiation encompasses the spectrum of ultraviolet (UV) radiation, visible (VIS) radiation, and near-infrared (nIR) radiation. The UV radiation has wavelengths in the spectrum between 100 nm and approximately 380 nm, the VIS radiation has wavelengths in the spectrum between approximately 380 nm and approximately 780 nm, and the nIR radiation has wavelengths in the spectrum between 780 nm and approximately 1400 nm. There are transition regions for all these spectra.

Within the meaning of the present invention, the medical-cosmetic effect may be considered to be achieved when a physiological or subjective emotional effect occurs. This may include tanning of the skin, for example, as is the case for UV-A and/or UV-B radiation, or also a beneficial heating effect, or vasodilation that results in better blood circulation in the skin, which occurs with irradiation in the near-infrared range, for example. Such an effect from medical-cosmetic radiation is likewise achieved by psychosomatic effects, in which particular light spectra may have an influence on the emotional state.

The device according to the invention includes at least one first illuminant for generating the stated medical-cosmetic, in particular optical, radiation.

The device further includes at least one first ventilation flow for cooling the at least one illuminant. Depending on the technology used for the illuminant, some other cooling of the illuminant may be necessary. With conventionally used mercury vapor lamps, much more heat is generated compared to LED illuminants, for example. Accordingly, the first ventilation flow for cooling the at least one illuminant may be adapted to the requirements of the illuminant. This ventilation flow is particularly preferably designed in such a way that it essentially flows past the illuminant.

In one particular embodiment, heat exchanger elements are provided which protrude into the first ventilation flow and facilitate heat dissipation from the first illuminant. Such heat exchangers are basically known to one skilled in the art, and may have surface-enlarging lamella structures or grid structures which the first ventilation flow may flow around better, thus facilitating dissipation of the heat from the illuminant.

The illuminants are particularly preferably low-pressure tubes.

In addition, the device according to the invention includes a first ventilation flow for cooling the at least one illuminant.

Within the meaning of the present invention, a ventilation flow may be understood to mean a completely fluid-connected arrangement of lines, and elements that are functionally placed in the line routing, via which a ventilation stream may be guided and influenced. The ventilation flow is particularly preferably designed in such a way that it draws in comparatively cooler air at an inlet, and discharges comparatively heated air at an outlet. Between the inlet and the outlet, this ventilation flow would be led past the elements being cooled, for example the illuminants. Warmer air that is generated by the elements to be cooled is led by the ventilation flow to the outlet and discharged.

Within the meaning of the present invention, the actual fluid flow in a ventilation flow, i.e., generally air that is moved by the ventilation flow, may be understood as a ventilation stream.

The device according to the invention further includes a second ventilation flow for cooling the human body or portions of the human body. This second ventilation flow may likewise preferably be fed with air outside the heated area of the device. This second ventilation flow particularly preferably also includes nozzles that lead the ventilation stream in question to the human body or portions of the human body to be cooled.

In one particular embodiment, the second ventilation flow is physically separate from the first ventilation flow. This may mean that there is essentially no fluid connection between the second ventilation flow and the first ventilation flow.

Furthermore, the device according to the invention includes at least one disinfection chamber, which is likewise in fluid connection with the second ventilation flow and is designed for physical disinfection of the second ventilation flow.

In one particular embodiment, the device according to the invention includes at least one air conditioner that is in fluid connection with the second ventilation flow. The air conditioner is designed to treat the ventilation flow in a climate-controlled manner.

Within the meaning of the present invention, an air conditioner may be designed to set one or more parameters of the ventilation stream that is conveyed in the second ventilation flow. The air conditioner is particularly preferably designed to set the temperature. In one particularly preferred embodiment, the climate-controlling treatment therefore encompasses lowering the temperature.

In a further particular embodiment, the climate-controlling treatment of the ventilation flow also includes a humidification function and/or a heating function. In one particular embodiment, the device according to the invention includes a plurality of disinfection chambers. The disinfection chambers are particularly preferably situated in series in a second ventilation flow, so that a ventilation stream in the second ventilation flow flows through the plurality of disinfection chambers.

Within the meaning of the present invention, a disinfection chamber is in fluid connection with a ventilation flow, for example, when a ventilation stream, i.e., air flowing through the ventilation flow, is able to pass through the disinfection chamber.

The disinfection chamber is particularly preferably in fluid connection with the second ventilation flow in such a way that a ventilation stream must pass through the disinfection chamber on its way through the second ventilation flow.

Within the meaning of the present invention, a ventilation stream may be understood to mean an air flow that is generatable by one or more turbomachines. Fans, for example, are suitable turbomachines.

In one particular embodiment, the physical disinfection is based on radiation, particularly preferably UV radiation, in particular UV-C radiation.

In one particular embodiment, the disinfection chamber includes a second illuminant. This illuminant is designed to emit UV radiation that is suitable for disinfection. This second illuminant is particularly preferably designed to emit radiation in the range of UV-C radiation, in particular in a wavelength range between 200 nm and 300 nm, more preferably between 220 nm and 260 nm, in particular from 254 nm to 255 nm.

In one particular embodiment, the disinfection chamber is designed in such a way that it defines a disinfection volume. The disinfection volume is the region of the disinfection chamber that may be acted on essentially completely by a physical disinfectant, in particular that may be acted on by UV-C radiation.

In one simple embodiment, the disinfection chamber may include a centrally situated second illuminant, for example a UV-C lamp. The entire space around this illuminant may be acted on by the UV-C radiation. The UV-C radiation acts as a physical disinfectant, and is suitable for reducing a number of possible infectious agents. UV-C radiation is particularly suitable for rendering microorganisms harmless by causing DNA and RNA damage in these organisms, and thus reducing the infection potential from bacteria, viruses, fungi, and other possible pathogens.

In one particularly preferred embodiment, the second illuminant is a mercury vapor-based illuminant that is designed to emit a wavelength with a 253.7 nm peak. Other suitable illuminants may include UV-C LEDs, which are designed to emit in a UV-C range between 250 nm and 290 nm, for example. Such illuminants may be designed to emit an overall narrow spectrum having a distinct peak in the stated range.

In one particular embodiment, a disinfection chamber according to the invention includes a plurality of illuminants, for example a plurality of the stated mercury vapor lamps and/or a plurality of light-emitting diode arrays or a combination of the two, to allow appropriate physical disinfection. The disinfection chamber is particularly preferably designed in such a way that a ventilation stream passing through the disinfection chamber is exposed to the UV-C radiation for as long as possible.

In one particular embodiment, the disinfection chamber includes a fluid guide that has at least one fluid inlet and at least one fluid outlet. The fluid guide is designed to lead a ventilation flow past the stated physical disinfectant in such a way that essentially the entire ventilation flow that is led past enters into an effective range of the physical disinfectant. The fluid inlet and/or the fluid outlet may be further designed in such a way that the UV-C radiation is retained as completely as possible within the disinfection chamber.

In one particular embodiment, the disinfection chamber therefore includes at least one light trap. In particular, the disinfection chamber includes at least one first light trap at a fluid inlet of the disinfection chamber and/or at least one second light trap at a fluid outlet of the disinfection chamber.

In one particular embodiment, a light trap within the meaning of the present invention includes a grid arrangement at the fluid inlet or fluid outlet. The grid arrangement may be multiple series of recesses made in alternation at a metal plate, which in the flow direction are covered in each case by a subsequent metal plate. The light trap is particularly preferably formed from two metal plates having offset recesses. A fluid flow is decelerated at a first metal plate and flows into the corresponding recesses in the first metal plate, and at the second metal plate once again strikes the metal plate, which it must flow around due to the second recesses. This has a number of advantages. With the light traps in question, it is possible not only to swirl the ventilation stream at the fluid inlet, for example, and at the fluid outlet in such a way that the impingement by the UV-C radiation on a quantity of air in question is maximized, but also to protect sensitive components in the device from the UV-C radiation.

As an alternative and/or in addition to the grid, corresponding perforation with offset holes in a metal plate may produce the same effect.

In one particular embodiment, the fluid inlet or fluid outlet includes a plurality of such metal plates, i.e., more than two such metal plates.

In one particular embodiment, the device according to the invention includes at least one first turbomachine for generating a first ventilation stream in the first ventilation flow, and at least one second turbomachine for generating a second ventilation stream in the second ventilation flow. Suitable turbomachines may be fans, for example.

In one particular embodiment, the device according to the invention includes at least one fragrance. The fragrance is preferably in fluid connection with the second ventilation flow and is designed to dispense a fragrance to the second ventilation stream.

In one particular embodiment, the fragrance is situated downstream from the disinfection chamber. The fragrance may include, for example, an area through which flow may pass, where scent molecules may be received by convection with the aid of a ventilation stream. For example, volatile organic compounds are suitable as scent molecules. These scent molecules may be suitable, for example, for leading a scent that is associated with freshness to the user via the ventilation stream. The dispensing of fragrances may likewise be suitable for masking undesirable odors or human body odors. If the dispensing of the fragrance is downstream from the disinfection chamber, there is no risk of the UV-C radiation in the disinfection chamber adversely affecting the fragrance. Ozone, among other things, may be generated when air is acted on by UV-C radiation. This may result in organic compounds being altered.

In contrast, if in one alternative embodiment the fragrance is in fluid connection upstream from the disinfection chamber, it may be ensured, for example by selecting fragrances that are photochemically stable and not impaired by reaction with ozone, that the fragrances are not adversely affected by the impingement with UV-C radiation in the fragrance chamber.

In one particular embodiment, the device according to the invention includes a supply container for accommodating a fragrance. The fragrance may be present in the form of a solid, for which the scent molecules go into the ventilation stream via sublimation, or in the form of a liquid, for which scent molecules are received from the ventilation stream via convection. Depending on the fragrance selected, it may be appropriate to heat it for use.

Accordingly, for example heating means may be provided to bring the fragrance to the required operating temperature.

In one particular embodiment, the disinfection chamber is situated upstream from the air conditioner in the flow direction of the second ventilation stream. It may thus be ensured that the number of active pathogens in the air conditioner is reduced. This may, for example, increase the service life of an air conditioner and reduce the necessary maintenance intervals, and in general may result in more reliable operation of the air conditioner.

In one alternative and/or supplemental embodiment, the disinfection chamber is situated downstream from the air conditioner in the flow direction of the second ventilation stream.

In one particular embodiment, the disinfection chamber includes a fluid guide. The fluid guide is designed to lead the second ventilation stream through the disinfection chamber in the longest, most winding and branch-free manner possible. For this purpose, the fluid guide must be essentially transparent to UV-C radiation. Suitable Plexiglas materials that are permeable to UV-C radiation are known to one skilled in the art. One possible arrangement may be a spiral coil, for example, that winds toward a midpoint. The illuminant may be situated at this midpoint, for example. In parallel with the first winding, a second winding winds outwardly from this midpoint to a fluid outlet. It may thus be ensured that a fluid, i.e., a ventilation stream, must cover a maximum path through the disinfection chamber that is as long as possible, thus maximizing the exposure to UV-C radiation so that a better degree of disinfection may be achieved.

In one particular embodiment, the disinfection chamber includes at least one reflector for reflecting optical radiation. At least one, in particular the entire, inner surface of the disinfection chamber, or all surfaces facing the illuminants, particularly preferably has/have a reflective design. The efficiency of the illuminant is thus increased.

In one particular embodiment, the device according to the invention includes at least one exhaust outlet for discharging the ventilation stream of the first ventilation flow.

In addition, the device according to the invention includes at least one vent outlet for cooling the human body or portions of the human body. The at least one vent outlet is particularly preferably suitable for guiding a ventilation stream onto the body or portions of the body in question.

In a further particular embodiment, the vent outlet is adjustably situated so that a desired ventilation stream may be set by the user. A plurality of vent outlets are particularly preferably situated around the human body or portions of the human body. If these vent outlets also have a controllable design, a user may set venting that is optimal for him/her by adjusting the vent outlets. For this purpose, for example the flow rate of individual vent outlets may have a controllable design. As a whole, this may result in an entire ventilation stream that is distributed over a plurality of vent outlets. If individual vent outlets are closed or down-regulated, the flow rate of the other vent outlets may be increased. Likewise, the orientation of the vent outlets may be adjustable, so that a ventilation flow from these vent outlets may be directed to the desired location.

In one particular embodiment, the device defines a treatment space in which the human body or portions of the human body is/are situated while being acted on by medical-cosmetic radiation. In a tanning bed, for example, the treatment space may be formed by a lying surface, a seating surface, and/or a standing surface with an associated cover. In an open state, the cover, which is openable via a hinge, is in an open position. If a user lies or positions him/herself in the treatment space and closes the cover, a defined treatment space forms that is defined over a specified volume.

In one particularly preferred embodiment, the treatment space with ventilation streams is insulated against the entry of air that does not originate from the second ventilation flow. For this purpose, for example air cylinders or air curtains may be provided which, via vent outlets, define a treatment space in such a way that only air originating from the ventilation stream may re-enter the treatment space. Thus, for example, vent outlets that are peripherally arranged around a treatment space may be provided which, due to their flow, form a barrier against incoming air from the outside. It may thus be ensured that during a treatment period, only disinfected air enters the treatment space. Suitable air curtains or air cylinders may be easily set up with the aid of corresponding lamella arrangements and by using nozzles. Thus, for example, air outlet nozzles having hollow cavities at the outer nozzle profile may be suitable for forming the air curtains in question and defining the treatment space.

In one particular embodiment, the device according to the invention includes at least one third illuminant for acting on a treatment space and/or surfaces of the treatment space in which the human body or portions of the human body are situated while being acted on by medical-cosmetic radiation, using UV radiation in a wavelength range between 207 nm and 222 nm, in particular 222 nm. This wavelength range is suitable for inactivating harmful microorganisms, and is essentially safe for human skin. With this arrangement, it is possible to additionally ensure disinfection of the surfaces. Examples of suitable third illuminants include excimer illuminants, which electrically excite fluorinated noble gases, resulting in a light-emitting plasma.

In one particular embodiment, the treatment space is defined by a capsule that is suitable for accommodating a human body or portions of a human body. The capsule may be designed in particular to accommodate the upper body, particularly preferably at least the head. In one particular embodiment, the capsule is equipped with noise-reducing elements to damp ambient noise, and/or with speakers.

In one particular embodiment, the device according to the invention is a relaxation capsule including illuminants and an illuminant control that is designed to carry out a relaxation program. For this purpose, the illuminant control may be designed, for example, to play a relaxation-inducing light program, for example a twilight effect. The capsule may be used to generate safe ambient air using disinfected air from the ventilation stream. Air curtains as described above may be provided at a capsule edge for assistance.

In one particular embodiment of the device according to the invention, the second ventilation flow includes at least one filter unit for filtering particles from a ventilation stream. This filter unit may be situated upstream from the disinfection chamber and/or downstream from the disinfection chamber. The filter unit is particularly preferably a high-efficiency filter for separating suspended particles from the air. In addition to the number of particles, such filters may also reduce the number of microorganisms, among other things, in the ventilation flow. Filter units that separate particles smaller than 1 μm are particularly preferably provided. Alternatively or additionally, the filter unit may include an active carbon filter. It is thus possible to bind volatile organic compounds, for example, which may also have a positive effect on the development of odors in the device.

In one particular embodiment, the device according to the invention includes a disinfection chamber, a filter unit with a high-efficiency filter, for example a HEPA high-efficiency filter, upstream from the disinfection chamber, and a filter unit with an active carbon filter downstream from the disinfection chamber. Following the filter unit with an active carbon filter, the device according to the invention may further provide a fragrance. By use of a device designed in this way, a treatment space for a patient may be provided that is completely hygienic, and that is accordingly also perceived this way by the treatment subject since neither unpleasant odors nor other organic compounds, and also pathogen reduction and a pleasant fragrance, are [present] in a ventilation flow for cooling the treatment subject.

In one particular embodiment, the device according to the invention includes a device housing that contains the illuminant and the two ventilation flows. The disinfection chamber is particularly preferably mounted inside the device housing. The air conditioner is likewise particularly preferably mounted inside the device housing. The housing may in particular be designed in such a way that an outer housing area is defined in which the exhaust air is led by the first ventilation flow. In one particular embodiment, the device housing may also be formed from a housing shell and a housing treatment surface. The housing treatment surface may be, for example, a lying surface or a transparent surface behind which the illuminant for impingement with medical-cosmetic radiation is situated. Vent outlets are preferably provided, via which a second ventilation flow may be led into the treatment space, i.e., into the effective range of the treatment subject and the human body or portions thereof.

For example, diagonal fans or radial fans, depending on the geometric configuration and placement in the device, may be provided as turbomachines. The geometric configuration and placement may be determined, depending on the situation, by one skilled in the art based on the design of the device and based on the positioning of the human body or portions thereof in the treatment space of the device.

A further aspect of the present invention relates to a method for operating a described device.

The method includes the initial step of providing a first ventilation flow for cooling the at least one illuminant.

The method further includes providing a second ventilation flow for cooling the human body or portions of the human body.

The method further includes carrying out the second ventilation flow through at least one air conditioner for climate-controlling treatment of the ventilation flow. This treatment may include cooling, for example. The treatment may also include a change in the moisture content of the ventilation flow.

The method according to the invention further provides for carrying out the second ventilation flow through at least one disinfection chamber together with means for physical disinfection of the second ventilation flow. It may thus be ensured that the treatment subject is always acted on by completely hygienic air. The cooling is perceived as pleasant, and the risk of contamination by potentially harmful pathogens and/or infectious agents is reduced. During operation, a device according to the invention would be suitable for medical-therapeutic purposes, for example for patients with a compromised immune system, as well as for the general public, in that, for example for tanning beds that are publicly used with a high frequency, it is to be ensured that infection by a disease-causing agent is excluded to the greatest extent possible. Overall, devices for acting on a human or portions of a human with medical-cosmetic radiation may thus be provided which are operable in a completely hygienic and safe manner.

The disinfection chamber is situated in such a way that the crucial ventilation flow, namely, the ventilation flow that comes through externally, i.e., from outside the device, into a treatment space, i.e., the space in which the treatment subject is accommodated, is disinfected. The disinfection chamber is situated in such a way that it does not impair the inner workings of the device.

In one particular embodiment of the method according to the invention, in addition the step of impinging a disinfection volume in the disinfection chamber with UV-C radiation is provided. The impingement takes place in such a way that a ventilation stream led through the disinfection chamber comes into the effective range of the UV-C radiation. By use of appropriate plates and an appropriate fluid guide, it may be ensured, for example, that the ventilation flow is reliably led past disinfectants.

In one particular embodiment, the disinfectant is at least one second illuminant that is designed to emit in the UV-C waveband. Accordingly, plates and guide units may be provided which ensure that the ventilation flow is led past this illuminant in such a way that it is led past completely in the effective range of the UV-C radiation. Appropriate plates may be further provided to maximize the residence time in the disinfection chamber. Appropriate geometric configurations that lead the ventilation flows through the disinfection chamber may be adaptively designed by one skilled in the art, depending on the volume that is present.

A further aspect of the present invention provides a disinfection chamber for upgrading devices for acting on a human body or portions thereof with medical-cosmetic radiation. In particular, the disinfection chamber involves upgrading devices for acting on a body with optical radiation.

The disinfection chamber includes at least one second illuminant with regard to the illuminant of the device, this second illuminant being designed to emit UV radiation that is suitable for disinfection. The illuminant is preferably designed to emit UV-C radiation. The disinfection chamber preferably includes a fluid guide that has at least one fluid inlet and at least one fluid outlet. The fluid guide is designed to lead a ventilation flow past the physical disinfectant in such a way that essentially the entire ventilation flow that is led past enters into an effective range of the physical disinfectant. In one specific example in which the illuminant emits UV-C radiation, this may be achieved, for example, in that the disinfection chamber includes an illuminant in the middle and at all surfaces at which the disinfection chamber is provided with adjoining reflectors. As a result, a space is created which comes to rest entirely in the effective range of the UV-C radiation emitted by the illuminant. A corresponding fluid inlet is used to blow fluid, conveyed by means of a fan, into this disinfection chamber. Such a fluid outlet is used to discharge the blown-in fluid from the disinfection chamber. The disinfection chamber according to the invention further includes at least one light trap, in particular at least one first light trap at a fluid inlet of the disinfection chamber, and/or at least one second light trap at a fluid outlet of the disinfection chamber. This light trap may be ensured, for example, by offsetting metal plates that are provided with ventilation slits, so that a ventilation slit recess of a first metal plate is not covered by a ventilation slit recess of a second metal plate. If the disinfection chambers in question are additionally equipped with reflectors, with this arrangement the efficiency of the illuminant on the fluid that is led through the disinfection chamber may be further increased.

The disinfection chamber according to the invention is placeable in a ventilation flow in such a way that a ventilation stream that is led by the ventilation flow is guided through the disinfection chamber.

The disinfection chamber according to the invention is suitable for retrofitting existing devices of the type stated at the outset, for example, and for improving the hygienic properties. This has a number of positive effects, not only with regard to the overall hygiene of the device, but also for the service life of an air conditioner, for example.

As the result of ultraviolet light not exiting from the disinfection chamber, the disinfection chamber may be placed at practically any location within the ventilation flow.

The disinfection chamber is particularly preferably placed in the area of the air conditioner in which the air is treated in a climate-controlled manner.

For one skilled in the art, it is self-evident that in an implementation according to the invention, all described embodiments may occur in any arbitrary combination with one another, provided that they do not mutually exclude one another.

The present invention is now explained in greater detail based on specific exemplary embodiments and the figures, but without being limited to same. For one skilled in the art, study of these specific exemplary embodiments may also show further advantageous embodiments and configurations of the present invention.

DESCRIPTION OF THE FIGURES

Exemplary embodiments of the invention are described with reference to the following figures. For the sake of simplicity, identical parts have been provided with the same reference numerals in the figures.

The figures schematically show the following.

DESCRIPTION OF THE INVENTION

Figure 1:
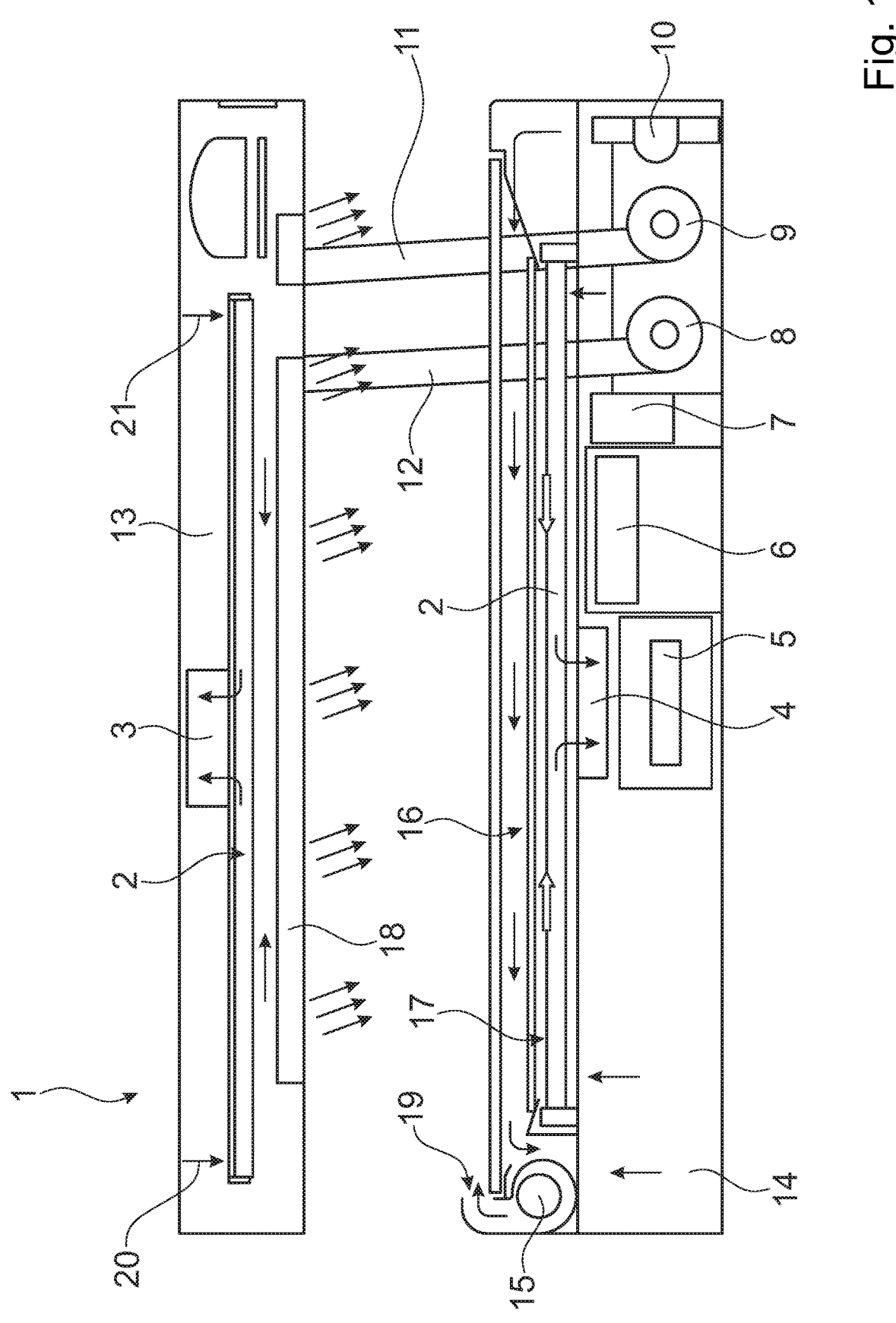
FIG. 1 shows a device according to the invention.

FIG. 1 shows an example of a device 1 according to the invention. In this case, the device 1 according to the invention is a tanning bed that is suitable for acting on a human with UV radiation, so that a tanning effect that is desired for cosmetic purposes occurs. The shown device 1 accordingly includes two illuminants 2 that are suitable for emitting UV radiation in a wavelength range that is harmless to health, for example UV light having wavelengths in the UV-A and UV-B range. For the shown device, low-pressure lamps that are suitable for emitting corresponding tanning radiation are particularly appropriate. The device 1 may be subdivided into two housing halves 13, 14, the components that are relevant for climate control being situated in the lower housing half 14, while the upper housing half 13 includes on the one hand an illuminant 2, and [on the other hand] the appropriate ventilation supply lines for cooling the illuminant and an exhaust air discharge unit 3. The upper housing half 13 also includes two vent inlets 20, 21 that draw in cooling air and discharge it via the exhaust air 3. The cooling air that is thus drawn in is led past the illuminant 2 and used for cooling the illuminant 2. Also provided in the upper housing half 13 is a second ventilation stream unit 18 that includes a plurality of nozzles which open into the treatment space (illustrated by arrows) and which may act on a patient in question with a cooling air flow. This second ventilation stream 18 is fed by the corresponding air conditioning in the lower housing half 14. For this purpose, the second ventilation stream has a flow connection 12 with a first fan 8 in the lower housing half 14. A second flow connection 11 is connected to a second fan 9 and is used to separately operate a head region. This may be advantageous, for example, when a ventilation stream is desired in the facial area which is different from the body area. In addition, colder cooling air may be desired in the facial area than in the body area. Temperature is perceived differently on the face than on the body. Also provided in the lower housing half 14 is a further main fan 5, which by means of a discharge outlet 4 leads air that is drawn into the lower housing half and led past the illuminant 2 and discharges it into an illuminant cooling space 17.

The lower housing half 14 also includes the air conditioner 6. Downstream from the air conditioner 6 is a disinfection chamber 7, as well as a first fan 10 that draws in fresh air from the outer area of the lower housing half for the second ventilation stream. The purified air from the air conditioner and the disinfection chamber 6, 7 is used by the first fan 8 and the second fan 9 to act on the user. Situated in the base area of the device 1 according to the invention is a further fan 15, which is connected to the disinfection chamber 7 via a fluid connection 16, and is connected to the air conditioner 6, and which likewise guides a disinfected ventilation flow 19 to the patient.

Figure 2:
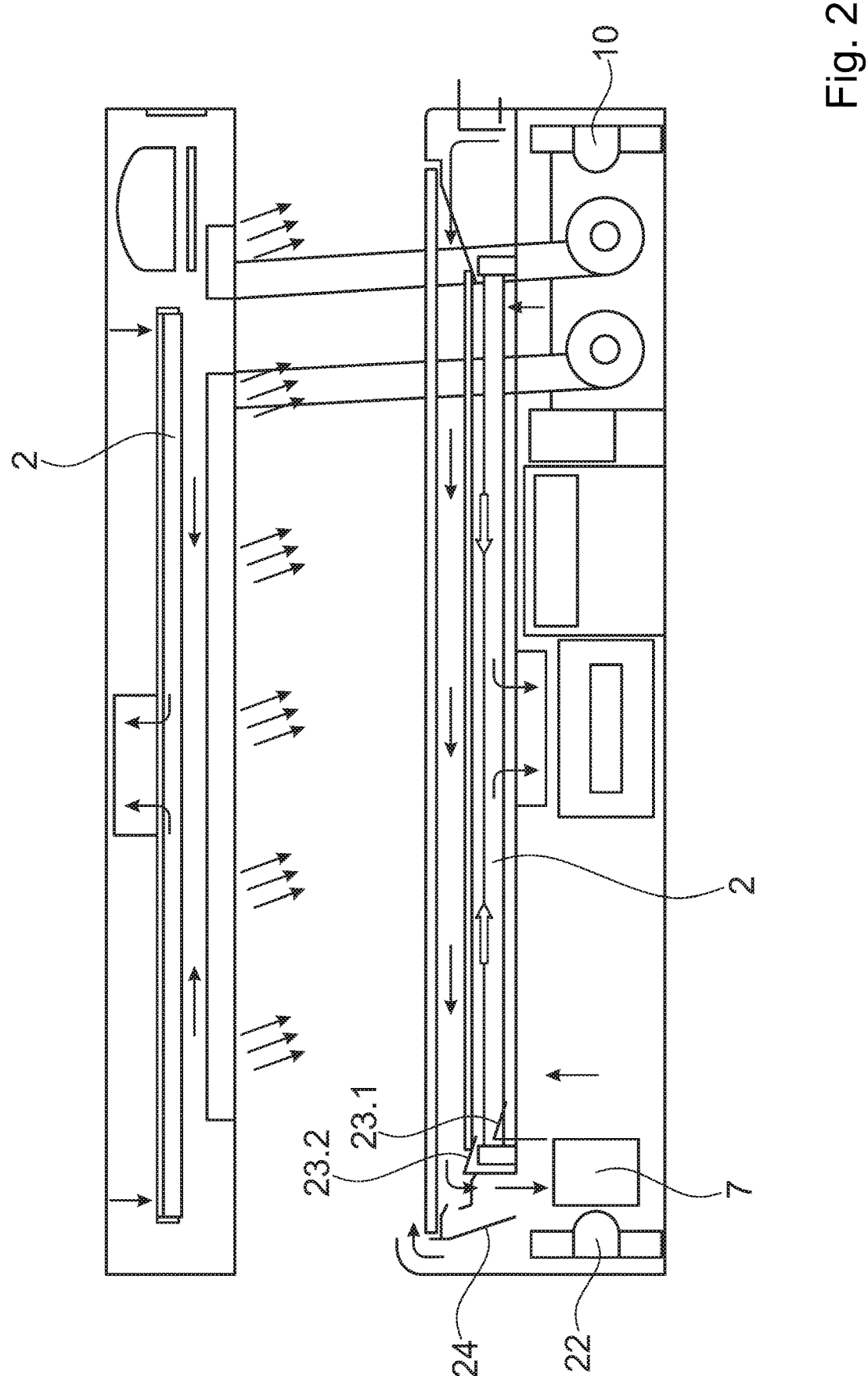
FIG. 2 shows a further device according to the invention.

In contrast to the embodiment from FIG. 1, the device in FIG. 2 is equipped with a second disinfection chamber 7. The device has a second fan 22, which in addition to the first fan 10 guides a fluid flow in the lower housing half and into the base area by means of a deflection baffle 24. In the present example, the device may also include a third ventilation flow that is separate from the second ventilation flow. For this purpose, the further fan 22 may be designed to draw in air from an exterior space. In the present example, no air conditioner in fluid connection with this ventilation flow is provided. However, it is also possible for the further fan to draw in air from the exterior space and to also be in fluid connection with an arrangement as shown in FIG. 1. In the present example in FIG. 2, this is illustrated by the arrows pointing from right to left, extending above the illuminant 2. These stand for air that is treated in a climate-controlled manner and disinfected, and that has been conveyed by the first fan across a first disinfection chamber and air conditioner, as already explained for FIG. 1.

The device in FIG. 2 is equipped with two disinfection chambers. Of course, further disinfection chambers may be provided, for example in the upper housing half. The disinfection chambers may have a fluid connection with the same ventilation flow, i.e., the second ventilation flow in the present example, or may be assigned their own ventilation flows, i.e., third, fourth, etc., ventilation flows on the fluid side. Similarly, multiple turbomachines may be provided.

Figure 3:
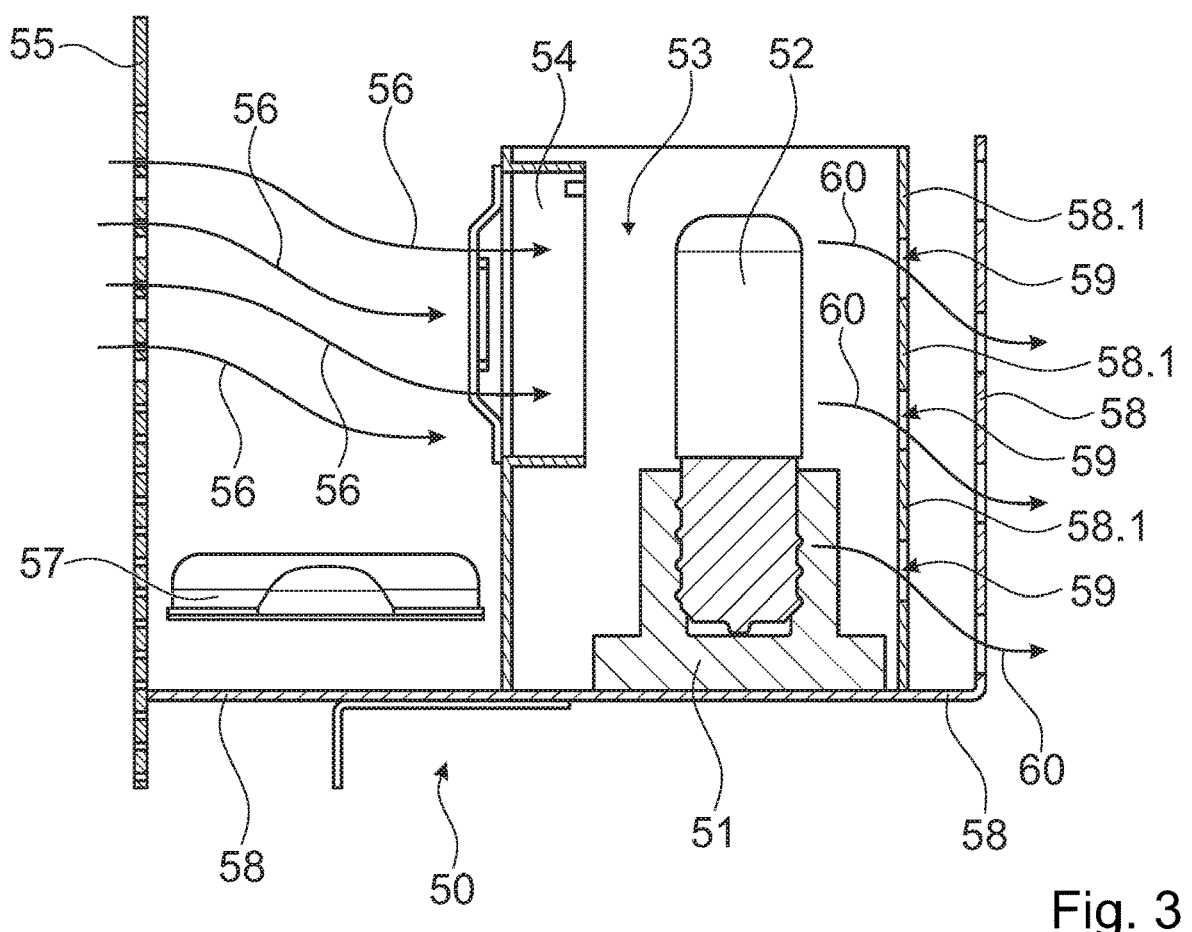
FIG. 3 shows a configuration of a disinfection chamber.

FIG. 3 shows how such a disinfection chamber may be implemented in a device according to the invention. In the present example, the ventilation stream schematically passes through the disinfection chamber from left to right; i.e., air passes into the disinfection chamber via a perforated plate 55 by means of a ventilation stream 56 by suction intake via a fan 54. The air passes through a fragrance 57 that is designed as a fragrance container 57, and delivers a corresponding odorant to the ventilation stream 56 via convection. The fragrance container 57 is situated on a retaining plate 58 that bears the entire fragrance chamber arrangement 50. Via the fan 54, which may be designed as an axial fan, the ventilation flow passes into the interior of the disinfection chamber, in the center of which an illuminant 52 is provided. In the present example the illuminant 52 is a UV-C lamp, for example a UV-C lamp that is suitable for emitting UV-C [radiation] with a peak at 254 nm. The UV-C lamp 52 is inserted into an E17 lamp socket 51. During operation, the UV-C lamp emits into a disinfection volume 53 of 450 UW/cm3. As a result, the air in the disinfection space 53 is disinfected. Accordingly, a disinfected ventilation flow 60 leaves the disinfection chamber via the fluid outlet 59. The present disinfection chamber is designed as a light trap in the fluid outlet area by providing an appropriately offset metal plate. Thus, the metal plate components 58.1 are each situated opposite from recesses, while the recesses 59 of the first metal plate are situated opposite from plate walls 58.

Figure 4:
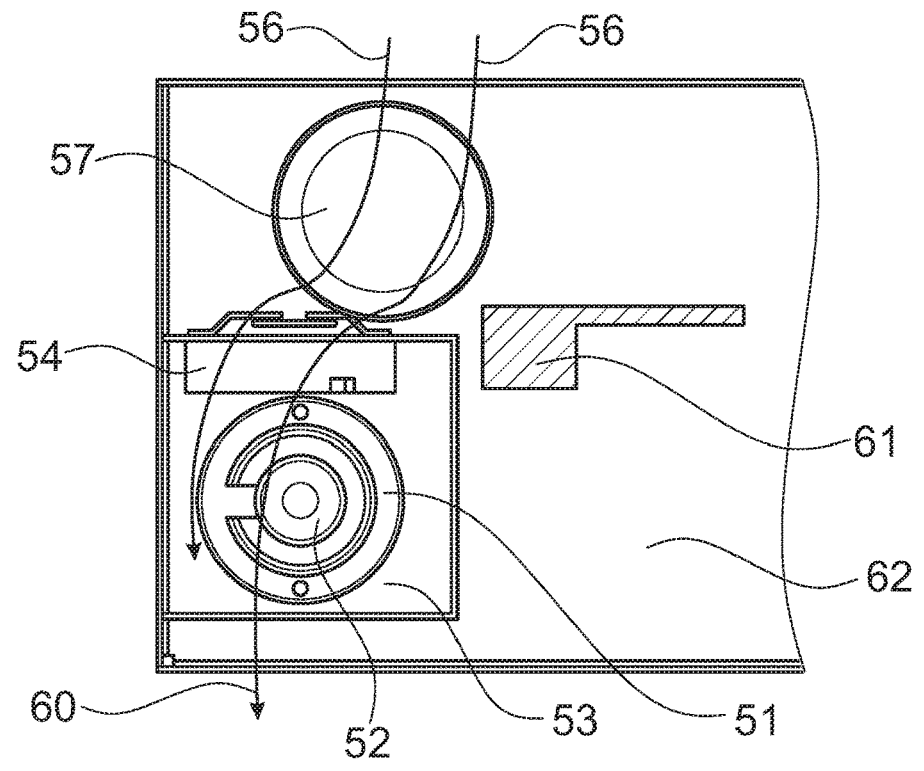
FIG. 4 shows the disinfection chamber from FIG. 3 in a top view.

The operating principle is further explained in FIG. 4. FIG. 4 shows the embodiment from FIG. 3 in a top view. A ventilation flow 56 moves past a fragrance 57, and via a fan 54 is drawn into the disinfection space 53 and into the effective range of a UV-C lamp 52. Accordingly, a substantially disinfected ventilation flow 60 leaves the disinfection chamber. Situated in the area 62 is a sensitive electronics system 61, which is largely protected from UV-C radiation by the arrangement of the metal plates designed as a light trap (see FIG. 3 above).

Figure 5:
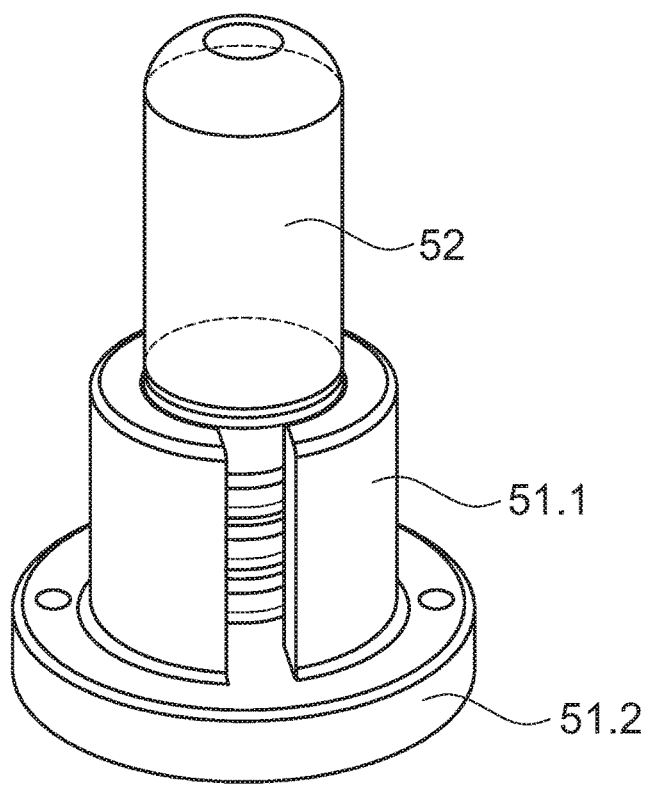
FIG. 5 shows a configuration of a suitable illuminant.

A suitable second illuminant is illustrated in FIG. 5; a UV-C light bulb 52 having a power of 3 W in an E17 thread 51.1 for an operating voltage of 10 to 11 V may emit a UV wavelength of 254 nm. The socket base 51.2 is arbitrarily placeable in a disinfection chamber. Thus, for example, a plurality of such illuminants may also be placed in a disinfection chamber.

Figure 6:
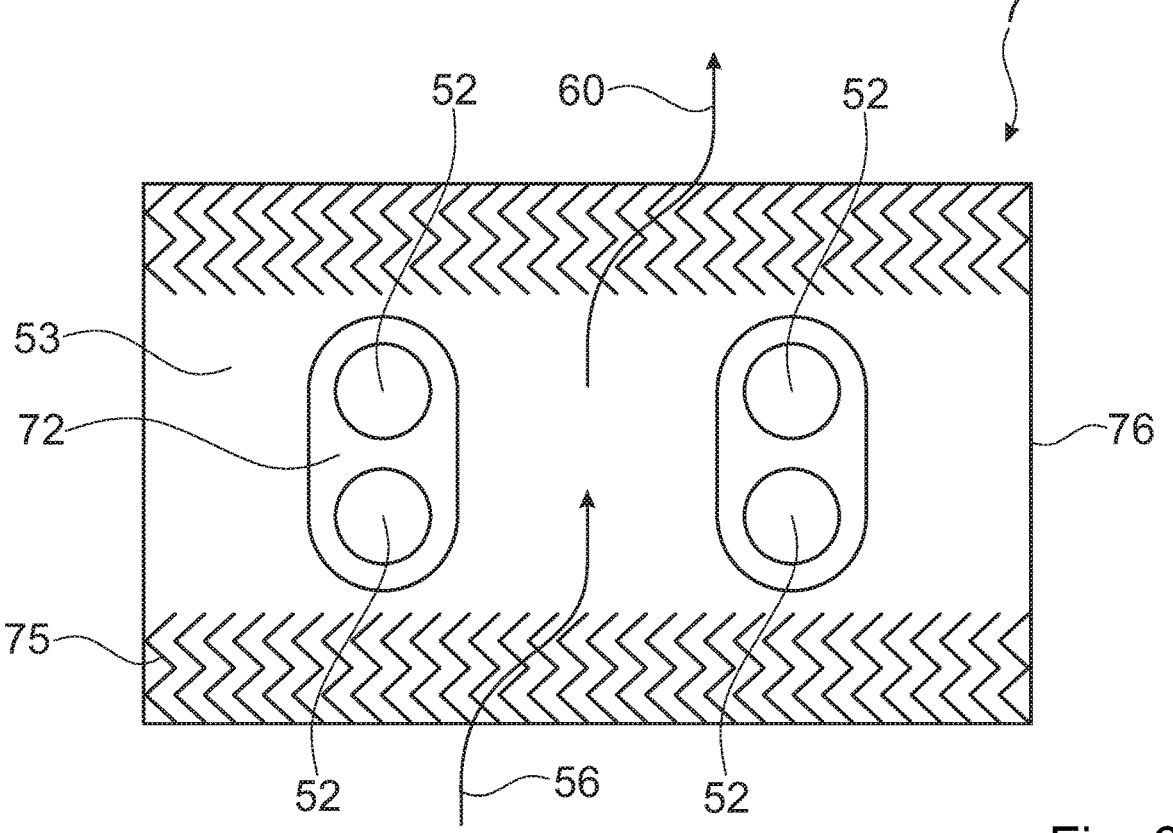
FIG. 6 shows an alternative design of a disinfection chamber.

An alternative design of a disinfection chamber 7 according to the invention is illustrated in FIG. 6. The disinfection chamber 7 has a disinfection chamber-housing 76, which in its interior defines a disinfection volume 53. For this purpose, the disinfection chamber housing may be [made up] of two continuous flat metal plates, and two metal plates that are provided with recesses and that may be brought into a fluid connection, preferably in the flow direction of a ventilation stream. In the present illustrated example, the metal plates provided with recesses are illustrated by an incoming ventilation flow 56 and an outgoing, disinfected ventilation flow 60. These metal plates are also provided with deflection elements 75 which on the one hand deflect the ventilation flows 56, 60, and on the other hand are used as a light trap, i.e., essentially hinder or prevent optical radiation that is emitted inside the disinfection chamber from escaping.

For outputting the optical radiation, a total of two illuminants 52 are provided, with two each being accommodated in a compact socket 72. In this example, the illuminants 52 are designed as two compact lamps 52. During operation, air to be disinfected flows downwardly, as incoming ventilation flow 56, into the disinfection chamber 7, and in the disinfection volume 53 is acted on by UV-C radiation in the wavelength range of 254 nm. The air, as disinfected ventilation flow 60, flows out of the chamber and may be used, for example, for cooling a user. The chamber may be designed in such a way that electrical contacts may be provided at the top or bottom in the observer plane in order to connect the lamp sockets to the electronics system of the accommodating device. Both illuminants 52 are inserted into a compact lamp socket 72, and may extend over essentially the entire chamber height, i.e., the extension of the disinfection chamber in the observer plane, in order to maximize the impingement by UV-C [radiation].

Figure 7:
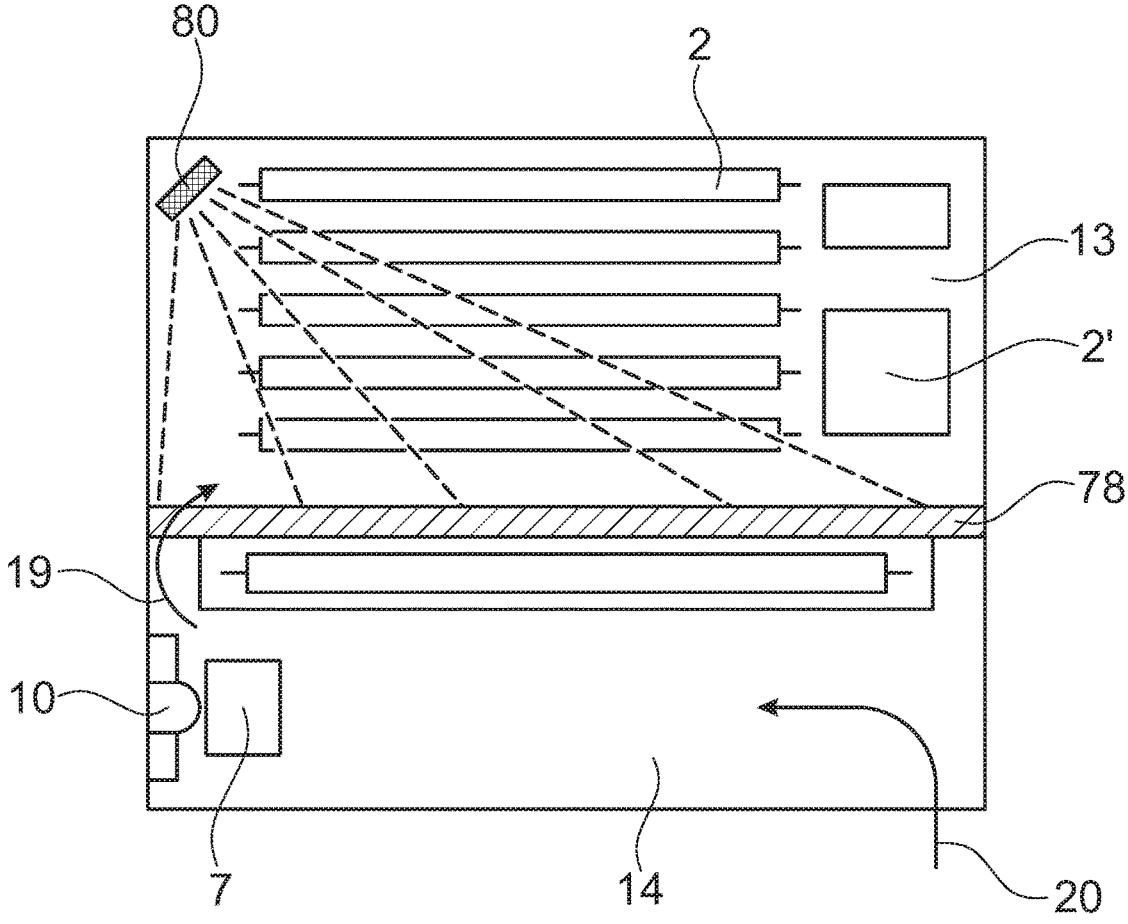
FIG. 7 shows a device according to the invention with additional surface disinfection.

FIG. 7 schematically shows a further device according to the invention for acting on a human body or portions of a human body with medical-cosmetic radiation. In this case, the device is designed as a tanning bed and accordingly has a first illuminant 2, which includes low-pressure tubes that are suitable for body tanning, and a further first illuminant 2', which includes a UV LED array that is suitable for facial tanning. In addition, infrared lamps, red light lamps, or nIR lamps may be provided, which have not been separately illustrated in the present example.

The device includes essentially two housing halves 13, 14, a lower housing half 14 and an upper housing half 13. For thorough tanning, illuminants 2, 2' are correspondingly [situated] in both housing halves 13, 14. During operation, a user would lie on a lying surface 78, which as a transparent window, i.e., a window that is permeable to UV radiation, is preferably made of Plexiglas, and would be acted on by tanning radiation on all sides by the illuminants 2, 2'. Combined UV-A/UV-B radiation sources are preferably used as illuminants, for example in a wavelength range between 280 nm and 400 nm.

The lower housing half 14 also includes means for cooling the user. In the present example, a first fan 10 is provided as a turbomachine which is in fluid connection with a ventilation inlet 20 that draws in cooling air. Likewise in fluid connection is a disinfection chamber 7 through which the drawn-in cooling air must flow before it is guided, as a disinfected ventilation flow 19, to the user.

This device includes surface disinfection in addition to air disinfection. In this regard, it is particularly important for surfaces that come into physical contact with the user to be disinfectable. For this purpose, this device has a third illuminant 80, which is used to act on the treatment space, in which the human body or portions of the human body is/are situated during the impingement by medical-cosmetic radiation, with UV radiation in a wavelength range between 207 nm and 222 nm, in particular 222 nm. The lying surface 78 is particularly preferably acted on by this third illuminant 80. One particular advantage of the 222 nm illuminant is that the UV-C radiation in this wavelength range is essentially unharmful to humans, while the disinfecting effect, i.e., the inactivation of potentially pathogenic agents, still occurs. Suitable third illuminants 80 include krypton chloride excimer lamps. Appropriate band filters may be used to largely exclude undesirable wavelengths. The third illuminant 80 thus assists with the disinfection of the treatment space, since the radiation that it emits has a pathogen-reducing effect on the air in the treatment space, in addition to the ventilation stream through the disinfection chamber.

The approach according to the invention provides completely hygienic use of devices for acting on a human body or portions thereof with medical-cosmetic radiation. The approach increases safety for the treatment subject for both medical and cosmetic use. The approach according to the invention is also installable in existing facilities as a retrofit option.

Further advantages will become apparent to one skilled in the art by a study of the particular embodiments.

The invention claimed is:

1. A device for acting on a human body or portions of a human body with medical-cosmetic radiation, including:
   a. at least one first illuminant for generating medical-cosmetic radiation;
   b. a first ventilation flow for cooling the at least one illuminant;
   c. a second ventilation flow for cooling the human body or portions of the human body, and
characterized in that the device further includes at least one disinfection chamber that is in fluid connection with the second ventilation flow and is designed for physical disinfection of the second ventilation flow.

2. The device according to claim 1, including at least one first turbomachine for generating a first ventilation stream in the first ventilation flow and/or at least one second turbomachine for generating a second ventilation stream in the second ventilation flow.

3. The device according to claim 1, wherein the disinfection chamber includes a second illuminant that is designed to emit UV radiation that is suitable for disinfection.

4. The device according to claim 1, wherein the disinfection chamber is designed in such a way that it defines a disinfection volume, and the disinfection volume may be acted on essentially completely by a physical disinfectant.

5. The device according to claim 1, wherein the disinfection chamber includes a fluid guide that has at least one fluid inlet and at least one fluid outlet, and the fluid guide being designed to lead a ventilation flow past a physical disinfectant in such a way that the entire ventilation flow that is led past enters into an effective range of the physical disinfectant.

6. The device according to claim 1, wherein the disinfection chamber includes at least one light trap.

7. The device according to claim 1, further including at least one air conditioner that is in fluid connection with the second ventilation flow and is designed to treat the ventilation flow in a climate-controlled manner.

8. The device according to claim 1, further including at least one fragrance that is in fluid connection with the second ventilation flow and is designed to dispense a fragrance to the second ventilation stream.

9. The device according to claim 7, wherein the disinfection chamber of the air conditioner is situated upstream from the second ventilation stream in the flow direction.

10. The device according to claim 7, wherein the disinfection chamber of the air conditioner is situated downstream from the second ventilation stream in the flow direction.

11. The device according to claim 1, wherein the disinfection chamber includes a fluid guide that is designed to lead the second ventilation stream through the disinfection chamber in a winding and branch-free manner, and the fluid guide being permeable to UV-C radiation.

12. The device according to claim 1, wherein the disinfection chamber includes at least one reflector for reflecting optical radiation.

13. The device according to claim 1, including at least one exhaust outlet for discharging the ventilation stream of the first ventilation flow, and at least one vent outlet for cooling the human body or portions of the human body.

14. The device according to claim 1, wherein the device defines a treatment space in which the human body or portions of the human body is/are situated while being acted on by medical-cosmetic radiation, and the treatment space with ventilation streams being insulated against the entry of air that does not originate from the second ventilation flow.

15. The device according to claim 1, further including at least one third illuminant for acting on a treatment space in which the human body or portions of the human body is/are situated while being acted on by medical-cosmetic radiation, using UV radiation in a wavelength range between 207 nm and 222 nm.

16. The device according to claim 1, wherein the second ventilation flow includes at least one filter unit for filtering particles from a ventilation stream.

17. A method for operating a device according to claim 1, including the steps:
   a. providing a first ventilation flow for cooling the at least one illuminant;
   b. providing a second ventilation flow for cooling the human body or portions of the human body; and c. carrying out the second ventilation flow through at least one disinfection chamber together with means for physical disinfection of the second ventilation flow.

18. The method according to claim 17, further including the step:

e. acting on a disinfection volume in the disinfection chamber with UV-C radiation in such a way that a ventilation stream led through the disinfection chamber comes into the effective range of the UV-C radiation.

19. The method according to claim 17, wherein the climate-controlling treatment of a ventilation stream includes cooling.

20. A disinfection chamber for upgrading devices for acting on a human body or portions thereof with medical-cosmetic radiation according to claim 1 wherein the disinfection chamber:

a. includes a second illuminant that is designed to emit UV radiation that is suitable for disinfection;

b. includes a fluid guide that has at least one fluid inlet and at least one fluid outlet, the fluid guide being designed to lead a ventilation flow past a physical disinfectant in such a way that essentially the entire ventilation flow that is led past enters into an effective range of the physical disinfectant;

c. includes at least one light trap; and wherein d. the disinfection chamber is placeable in a ventilation flow in such a way that a ventilation stream that is led by the ventilation flow is guided through the disinfection chamber.

\* \* \* \* \*